United States Patent
Hongo et al.

(10) Patent No.: US 7,306,576 B2
(45) Date of Patent: Dec. 11, 2007

(54) MEDICAL NEEDLE DEVICE WITH MIS-PUNCTUATION PREVENTION SHIELD

(75) Inventors: Susumu Hongo, Miyoshi (JP);
Takafumi Kiyono, Miyoshi (JP);
Kuniharu Moriwaki, Miyoshi (JP)

(73) Assignee: JMS Co., Ltd., Hiroshima (JP)

( * ) Notice: Subject to any disclaimer, the term of this patent is extended or adjusted under 35 U.S.C. 154(b) by 185 days.

(21) Appl. No.: 10/489,398

(22) PCT Filed: Jul. 4, 2003

(86) PCT No.: PCT/JP03/08550

§ 371 (c)(1),
(2), (4) Date: Mar. 10, 2004

(87) PCT Pub. No.: WO2004/004805

PCT Pub. Date: Jan. 15, 2004

(65) Prior Publication Data

US 2004/0249351 A1    Dec. 9, 2004

(30) Foreign Application Priority Data

Jul. 9, 2002 (JP) .............................. 2002-200385
Oct. 30, 2002 (JP) .............................. 2002-316459

(51) Int. Cl.
*A61M 5/00* (2006.01)
*A61M 5/32* (2006.01)

(52) U.S. Cl. ........................ 604/110; 604/198
(58) Field of Classification Search ................. 604/110, 604/192, 197, 198, 263, 164, 180, 171, 177, 604/195; 128/919

See application file for complete search history.

(56) References Cited

U.S. PATENT DOCUMENTS 4,170,993 A * 10/1979 Alvarez ..................... 604/180

(Continued)

FOREIGN PATENT DOCUMENTS

JP            1-212561            8/1989

(Continued)

*Primary Examiner*—Catherine S. Williams
(74) *Attorney, Agent, or Firm*—Hamre, Schumann, Mueller & Larson, P.C.

(57) ABSTRACT

In a medical needle device having a shield for reduction of needlestick injuries, a protrusion is formed on an outer peripheral surface of a hub to which a needle is mounted, a height of the protrusion being set so that the protrusion protrudes beyond an inner diameter of a shield tube, and a gate groove is formed at an inner surface of the shield tube to extend from a front end to the vicinity of a rear end, dimensions of the gate groove being such that the protrusion can fit in a front end portion of the gate groove. In a state where the protrusion is exposed from the front end of the shield tube, the hub can rotate with respect to the shield tube. At a rotational position of the protrusion at which it does not face a front end of the gate groove, a position of the hub is limited so as not to move toward a rear end side of the shield tube due to engagement of the protrusion with a front end face of the shield tube. At a rotational position of the protrusion at which it face the front end of the gate groove, the protrusion can slide into the gate groove, whereby the hub can move so that a tip of the needle can be stored in the shield tube. In the penetrating state of the needle that enables the puncturing, the needle cannot move in the shield for reduction of needlestick injuries and can rotate.

8 Claims, 5 Drawing Sheets

U.S. PATENT DOCUMENTS

| | | | |
|---|---|---|---|
| 4,425,120 A * | 1/1984 | Sampson et al. | 604/198 |
| 4,846,805 A * | 7/1989 | Sitar | 604/165.04 |
| 5,437,648 A * | 8/1995 | Graves et al. | 604/263 |
| 5,562,636 A | 10/1996 | Utterberg | |
| 5,779,679 A * | 7/1998 | Shaw | 604/158 |
| 5,928,199 A | 7/1999 | Nakagami | |
| 6,641,555 B1 * | 11/2003 | Botich et al. | 604/110 |
| 2004/0249346 A1 * | 12/2004 | Kunitomi et al. | 604/177 |

FOREIGN PATENT DOCUMENTS

| | | |
|---|---|---|
| JP | 5-300942 | 11/1993 |
| JP | 2000-288087 | 10/2000 |
| JP | 2001-293087 | 10/2001 |

* cited by examiner

FIG. 1
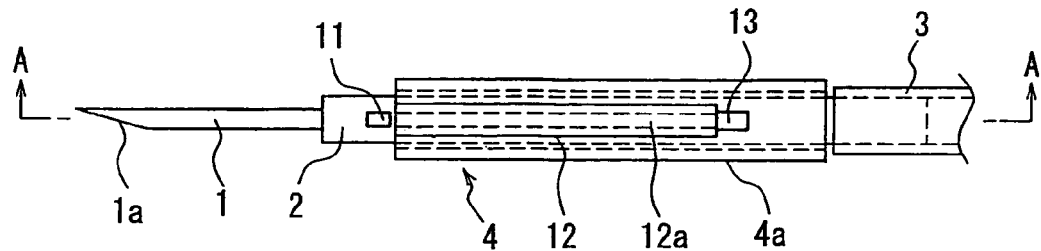
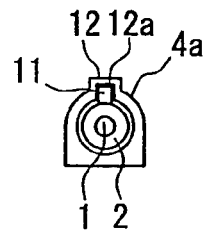
FIG. 2
FIG. 3A
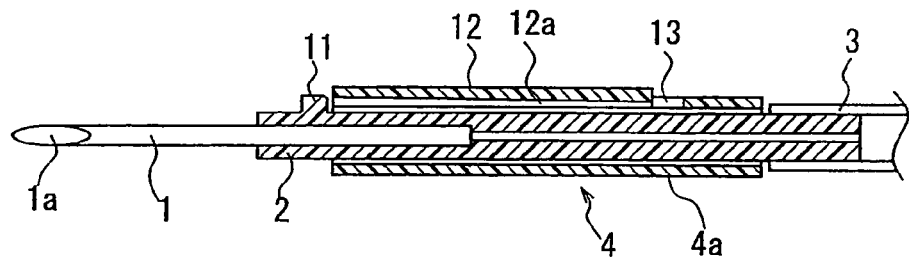
FIG. 3B
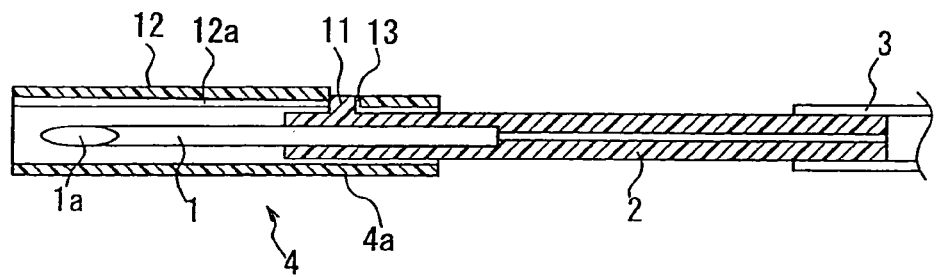

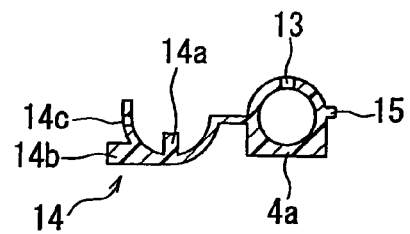
FIG. 6B
FIG. 7A
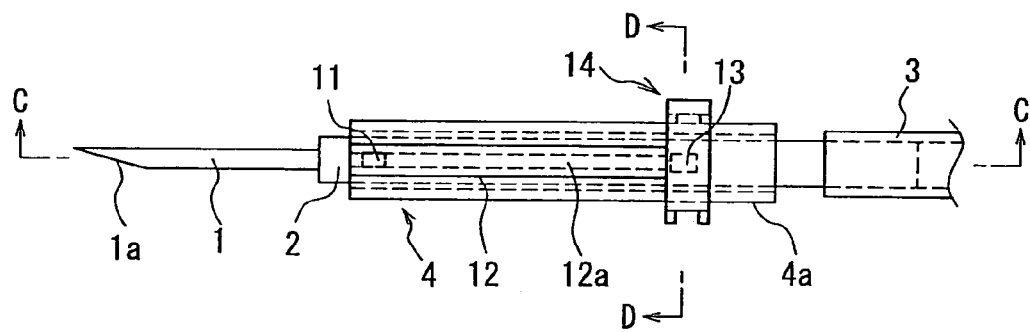
FIG. 7B
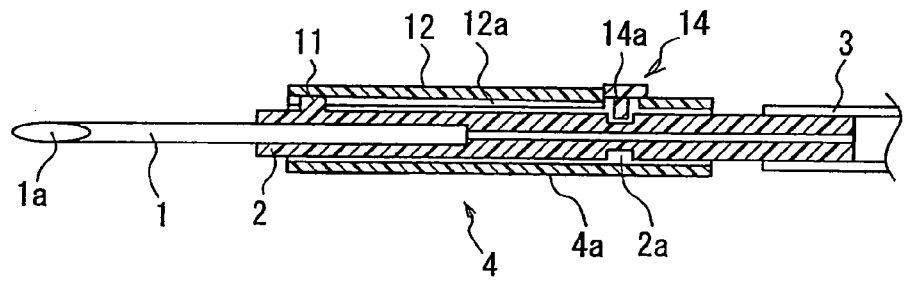
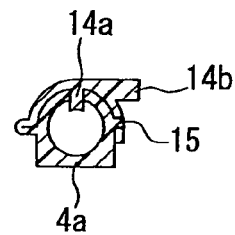
FIG. 7C

MEDICAL NEEDLE DEVICE WITH MIS-PUNCTUATION PREVENTION SHIELD

BACKGROUND OF THE INVENTION

1. Field of the Invention

The present invention relates to medical needle devices, and more particularly relates to medical needle devices having a shield for the reduction of needlestick injuries, in which a used needle can be stored safely.

2. Related Background Art

Conventionally, contamination and infections due to needlestick injuries with injection needles or puncture needles have been a problem in medical facilities. In particular, recently, as hepatitis B, hepatitis C, HIV (human immunodeficiency virus) and the like have received widespread attention, there is a strong demand for means that actively reduce such needlestick injuries.

As a means for preventing such needlestick injuries, a configuration in which a cylindrical shield is provided so that the shield can slide with respect to the injection needle is known. That is, depending on the sliding position of the shield, the injection needle is either exposed or it is contained in the shield. When disposing of a used injection needle or a used puncture needle, a needle is slid into the shield so as to be contained therein.

Injection needle devices described in JP H6(1994)-7861B, JP H5(1993)-300942A and U.S. Pat. No. 4,170,993 are known as examples of such configurations. These injection needle devices are a winged injection needle device that is used widely in a procedure such as a liquid infusion, a blood transfusion, extracorporeal blood circulation, or the like. In the winged injection needle device, the wings are attached to the outer peripheral surface of a slidable cylindrical shield, and the wings slide together with the shield on the outer side of the injection needle. In order to prevent needlestick injuries after use of the injection needle, the tip of the injection needle can be covered with the shield by sliding it.

In the course of using such an injection needle device having the cylindrical shield, a mechanism is necessary for limiting the position of the injection needle relative to the shield so as to maintain a predetermined state with the needle protruding from the shield. Especially, during the puncturing action, the injection needle should be held so as not to be pushed into the shield. In addition, after the puncturing action, in order to retain the puncturing state of the injection needle, the injection needle might be required to be held at a predetermined position relative to the shield. This is because, even when the shield is fixed to the punctured portion of the patient for preventing the injection needle from leaving the retained state, if the injection needle is easily moved within the shield, there is the risk that the injection needle comes off the punctured portion of the patient. Each injection needle device described in JP H6(1994)-7861B, JP H5-300942 A or U.S. Pat. No. 4,170, 993 has a configuration for holding a predetermined state of an injection needle relative to a shield.

Furthermore, at the time of storing the injection needle in the shield, it is desirable that the injection needle can slide easily with respect to the shield. In the case of the configuration described in JP H6-7861B, however, in order to store the injection needle in the shield, the injection needle has to be retracted in the shield against a holding force for holding the injection needle with respect to the shield while the holding force is still applied thereto. In the case of the configuration described in JP H5-300942 A, at the time of storing the injection needle in the shield, the force for holding the injection needle can be weakened. Due to its configuration, however, it is difficult to weaken sufficiently the force applied when the injection needle is stored in the shield while ensuring the sufficiently large force for holding the injection needle with respect to the shield. According to the configuration described in U.S. Pat. No. 4,170,993, such conditions can be satisfied.

In the injection needle device described in U.S. Pat. No. 4,170,993, however, a configuration for holding the injection needle forms an obstacle, which makes it difficult for the injection needle to rotate with respect to the shield in the usage state in which the injection needle protrudes from the shield.

In order to adapt to various operations suitably, it is desirable that, in the usage state in which the injection needle protrudes from the shield, the injection needle can rotate with respect to the shield. For instance, in order to make an angle of a blade surface of the needle after puncturing different from that during the puncturing, the injection needle has to be rotated. Also, in both of the configurations described in JP H6(1994)-7861B and JP H5(1993)-300942A, it is difficult to make the injection needle rotatable with respect to the shield in the usage state in which the injection needle protrudes from the shield.

Although the above problems are described referring to the example of the winged injection needle device, these problems arise commonly also in injection needle devices without wings.

SUMMARY OF THE INVENTION

Therefore, with the foregoing in mind, it is an object of the present invention to provide a medical needle device having a shield for the reduction of needlestick injuries, capable of limiting the position of a needle so as not to move in a shield from a usage state in which the needle protrudes from the shield, and capable of allowing the needle to rotate with respect to the shield in that state as well.

A medical needle device having a shield for reduction of needlestick injuries according to the present invention includes: the shield for reduction of needlestick injuries including a substantially cylindrical shield tube as a main body; a hub inserted into the shield tube so that the hub is movable in an axial direction and whose rear end portion can be connected to an infusion tube; and a needle mounted to a front end portion of the hub. A tip of the needle can be stored in an inner bore of the shield tube. The hub has a protrusion at a portion of an outer peripheral surface at a front end portion thereof, a height of the protrusion being such that the protrusion protrudes beyond an inner diameter of the shield tube. A gate groove is formed at an inner surface of the shield tube so as to extend from a front end to the vicinity of a rear end of the shield tube, the gate groove having dimensions such that the protrusion at the front end portion of the hub can fit in a front end portion of the gate groove. In a state where the protrusion is exposed from the front end of the shield tube, the hub can rotate with respect to the shield tube. At a rotational position of the protrusion at which it does not face a front end of the gate groove, a position of the hub is limited so as not to move toward a rear end side of the shield tube due to engagement of the protrusion with a front end face of the shield tube. At a rotational position of the protrusion at which it faces the front end of the gate groove, the protrusion can slide into the gate groove.

With this configuration, in the state of a needle protruding from the shield, the engagement of the protrusion with the front end face of the shield tube allows the needle to be held so as not to move in the shield. In addition, in that state, the needle can rotate with respect to the shield.

In the above configuration, preferably, the shield tube has an engagement hole that is formed adjacent to a rear end of the gate groove, a depth of the gate groove being set so as to be shallower than the height of the protrusion at a rear end portion of the gate groove, and the protrusion can slide along the gate groove so as to engage with the engagement hole. With this configuration, when the needle is stored in the shield tube, the needle can be held with respect to the shield tube securely.

The protrusion may be provided at a position that does not correspond to a side of a blade surface of the needle and its reverse side in a circumferential direction of the hub. With this configuration, when the needle is held so as not to move in the shield, the needle can be set in a state convenient for the puncturing action. As a result, an unexpected accident in which the needle retracts in the shield can be prevented.

The protrusion may be provided at a position that corresponds to a side of a blade surface of the needle in a circumferential direction of the hub. In this case, when the protrusion engages with the gate groove so as to make it impossible for the needle to rotate with respect to the shield, with a blade surface facing upwards, the protrusion is prevented from contacting with the punctured portion of the patient. Therefore, a state suitable for the puncturing can be obtained securely.

Preferably, the above medical needle device having a shield for reduction of needlestick injuries further includes: a latching strip having flexibility, provided so as to extend from a side wall of the shield tube; and a through hole provided in the shield tube so as to correspond to a position of the latching strip. The latching strip has a protrusion protruding toward a side direction, and when the latching strip is wrapped around the shield tube, the protrusion is inserted into the through hole so as to limit movement of the hub in the axial direction within the shield tube. This configuration enables the hub to be held in a predetermined state with respect to the shield tube.

In addition, it is preferable that the latching strip has a mechanism for holding the latching strip, functioning so as to hold the wrapped state of the latching strip around the shield tube.

The above-mentioned shield for reducing needlestick injuries may be a winged shield that further includes a pair of wings coupled near the front end of the shield tube.

Preferably, each of the wings has a wing protrusion formed so as to protrude from a wing surface, and the shield tube has through holes formed on side portions of a cylindrical wall so that wing protrusions can be inserted in the respective through holes. By superimposing both of the wings on the shield tube along a side surface of the shield tube, each wing protrusion can pass through the through hole so as to be inserted into the inner bore of the shield tube, so that each wing protrusion prevents the hub from moving in the axial direction within the shield tube, and so that the hub can be held with respect to the shield tube while keeping a state in which the needle protrudes from the front end of the shield tube by a predetermined length.

BRIEF DESCRIPTION OF THE DRAWINGS

FIG. 1 is a plan view of a medical needle device according to Embodiment 1 of the present invention.

FIG. 2 is a side view of the same medical needle device from a left side of FIG. 1.

FIG. 3A is a cross-sectional view taken along the line A-A of FIG. 1.

FIG. 3B is a cross-sectional view showing a state after a storing action is conducted on the device in the state of FIG. 3A.

FIG. 6B is a cross-sectional view taken along the line B-B of FIG. 6A.

FIG. 7A is a plan view showing an operation of the medical needle device of FIG. 6A.

FIG. 7B is a cross-sectional view taken along the line C-C of FIG. 7A.

FIG. 7C is a cross-sectional view taken along the line D-D of FIG. 7A.

DETAILED DESCRIPTION OF THE INVENTION

Embodiment 1

Figure 4A:
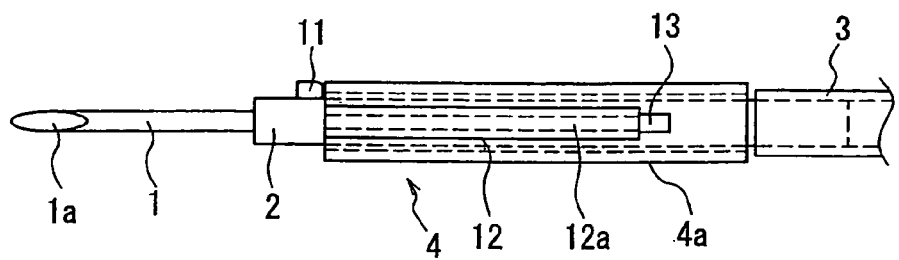
FIG. 4A is a plan view showing an operation of the medical needle device of Embodiment 1.

FIG. 1 is a plan view of a medical needle device according to Embodiment 1 of the present invention, and FIG. 2 is a side view of the medical needle device from a left side of FIG. 1. FIG. 3A is a cross-sectional view taken along the line A-A of FIG. 1. FIG. 3B is a cross-sectional view showing a state after a storing action is conducted on the device in the state of FIG. 3A.

Reference numeral 1 denotes a needle, which is fixed to a front end portion of a hub 2 made of resin. A tube 3 is connected to a rear end portion of the hub 2. Reference numeral 4 denotes a shield, including as a main body a shield tube 4a made of resin and having a substantially cylindrical shape. The hub 2 has a length such that a front end portion and a rear end portion thereof can protrude from the shield tube 4a when the hub 2 is inserted into an inner bore of the shield tube 4a. An outer diameter of the hub 2 has a size such that a slight gap can be formed between the hub 2 and an inner wall of the shield tube 4a so as to allow the rotation of the hub 2 with respect to the shield tube 4a and the movement of the hub 2 in an axial direction.

On the front end portion of the hub 2 that is exposed from a front end of the shield tube 4a, a protrusion 11 is formed at a portion of its outer peripheral surface. A height of the protrusion 11 from the outer surface of the hub 2 is, as shown in FIG. 2, set so that the protrusion 11 protrudes beyond the inner diameter of the shield tube 4a. On an outer surface of the shield tube 4a, a ridge portion 12 is formed, as shown in FIG. 1, so as to extend in the axial direction from the front end to the vicinity of a rear end of the shield tube 4a. On an inner wall of the ridge portion 12, a gate groove 12a is formed to extend in the axial direction from the front end to the vicinity of the rear end of the shield tube 4a. The gate groove 12a has dimensions such that the protrusion 11 can enter through a front end portion of the gate groove 12a. An engagement hole 13 is formed adjacent to a rear end of the gate groove 12a so as to penetrate the wall of the shield tube 4a. The engagement hole 13 has dimensions so as to allow the engagement with the protrusion 11. The ridge portion 12 is not necessarily provided for forming the gate groove 12a. If the shield tube 4a is thick enough, the gate groove 12a may be formed directly at the inner wall of the shield tube 4a.

As is evident from FIG. 3A, the protrusion 11 can enter through the front end of the gate groove 12a so as to slide along the gate groove 12a. Furthermore, as shown in FIG. 3B, the protrusion 11 can pass through the rear end of the gate groove 12a so as to engage with the engagement hole 13. In this state, a tip of the needle 1 is stored in the inner bore of the shield tube 4a.

The gate groove 12a is tilted so that a depth from an inner wall surface of the shield tube 4a becomes shallower toward the rear end and so that the depth at the rear end becomes smaller than the height of the protrusion 11. Therefore, in the course of sliding of the protrusion 11 along the gate groove 12a, a top surface of the protrusion 11 contacts with a bottom surface of the gate groove 12a by an increasing force with increasing proximity to the rear end. Thus, when the protrusion 11 passes through the rear end of the gate groove 12a, the protrusion 11 is elastically deformed to be compressed in the height direction. As a result of the engagement with the engagement hole 13, the compressive pressure is released, so that the height of the protrusion recovers. In this state, the contact of a front end face of the protrusion 11 with a rear end face of the ridge portion 12 makes it impossible for the protrusion 11 to move to the front end side, i.e., to move backward. At the same time, the contact of a rear end face of the protrusion 11 with a rear end face of the engagement hole 13 prevents the protrusion 11 from moving toward the rear end side. In this way, the engagement of the protrusion 11 with the engagement hole 13 can provide a function for locking the hub 2 with respect to the shield tube 4a. As a result, the state of the needle 1 being stored in the shield tube 4a can be kept, so that a state for avoiding needlestick injuries can be provided. The tile of the gate groove 12a may be provided at the total length or at the rear side portion.

Figure 4B:
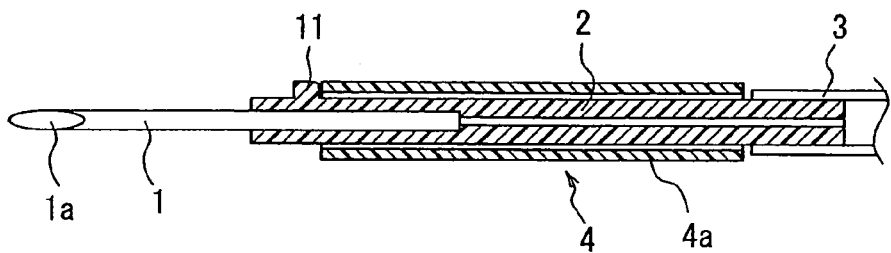
FIG. 4B shows a cross-section of the state of FIG. 4A.

As is evident from these configurations, when the protrusion 11 shown in FIG. 1 is exposed from the front end of the shield tube 4a, the hub 2 can rotate with respect to the shield tube 4a. With this configuration, as shown in FIG. 4A, the protrusion 11 can have a state of protruding in the side direction of the shield tube 4a. FIG. 4B shows a cross-section of the state of FIG. 4A. Since the hub 2 can rotate with respect to the shield tube 4a, a rotational position of a blade surface 1a of the needle 1 can be adjusted freely relative to the shield 4, so as to be adaptable to various operations to be conducted after the puncturing action.

In the state of FIG. 4A, the protrusion 11 does not face the front end of the gate groove 12a. At this rotational position, the engagement of the rear end face of the protrusion 11 with the front end face of the shield tube 4a prevents the hub 2 from moving toward the rear end side. Therefore, during the puncturing action, for example, by adjusting the rotational position of the protrusion 11 to such a position, a state of the needle 1 can be held so as to protrude from the shield tube 4a and so as not to be pushed into the shield tube 4a.

As stated above, in the usage position in which the needle 1 protrudes from the front end of the shield tube 4a by a predetermined length, the engagement of the protrusion 11 with the front end face of the shield tube 4a limits the position of the hub 2 with the needle 1 attached thereto, within the shield tube 4a. In addition, the contact of an end face of the tube 3 with the rear end of the shield tube 4a prevents the hub 2 from further moving in the direction toward the front end of the shield tube 4a. With this configuration, the position of the needle 1 can be limited so as not to protrude from the shield tube 4a by the predetermined length or more. As a result of these configurations, a function for holding the hub 2 at the usage position can be obtained.

To dispose of the medical needle device after usage, the rotational position of the protrusion 11 is adjusted so as to face the gate groove 12a, whereby the hub 2 can move easily toward the rear end side of the shield tube 4a and, as shown in FIG. 3B, can be retained in that position.

Figure 5:
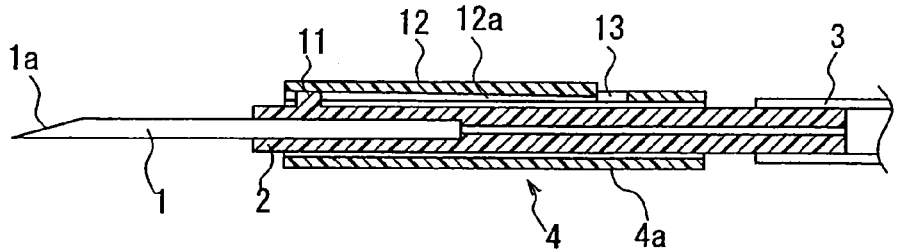
FIG. 5 is a cross-sectional view showing another embodiment of the medical needle device according to Embodiment 1.

The positional relationship between the protrusion 11 and the blade surface 1a of the needle 1 in the circumferential direction of the hub 2 may be set depending on an intended use. For instance, in FIG. 4A, the protrusion 11 is provided at a position that forms an angle of 90° with the blade surface 1a of the needle 1 in the circumferential direction of the hub 2. In this way, the protrusion 11 can be provided at the position that does not correspond to a side of the blade surface 1a and its reverse side, whereby the needle 1 can be set in a state convenient for the puncturing action while the needle 1 can be kept so as not to move in the shield tube 4a. As a result, unexpected accidents such as the needle 1 being retracted in the shield tube 4a from the puncturing state can be prevented. Alternatively, as shown in FIG. 5, there may be a case where the protrusion 11 at the position that corresponds to the blade surface 1a is convenient. In such a case, by engaging the protrusion 11 with the gate groove 12a so that the needle 1 cannot rotate with respect to the shield tube 4a, the protrusion 11 does not contact with the punctured portion of the patient when the blade surface 1a faces upward. Therefore, a suitable state for the puncturing can be obtained with reliability.

The above-described embodiment exemplifies the case where the device includes one protrusion 11 and one gate groove 12. However, the device can include a combination of one or two protrusions 11 and two gate grooves 12.

Figure 6A:
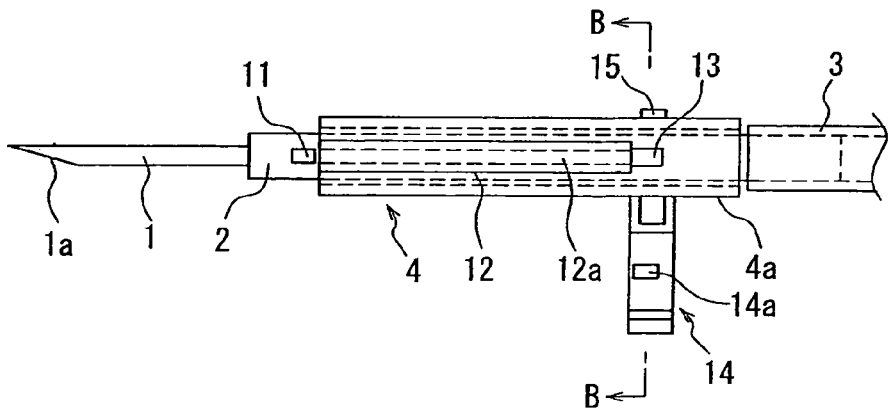
FIG. 6A is a plan view showing an improved example of the medical needle device of FIG. 1.

In addition to the above-described basic configuration, as shown in FIG. 6A, a holding mechanism can be provided additionally for latching the hub 2 with respect to the shield tube 4a. FIG. 6B is a cross-sectional view of the shield tube 4a taken along the line B-B of FIG. 6A. Reference numeral 14 denotes a latching strip that makes up the holding mechanism. The latching strip is provided to extend from a side wall of the shield tube 4a and has flexibility. The latching strip 14, as shown in FIG. 6B, has a substantially arc shape, in which a protrusion 14a and a grasping rib 14b are formed. At a front end portion of the latching strip 14, an engagement hole 14c is formed. On a side wall of the shield tube 4a, a fixing protrusion 15 is formed on the opposite side of the latching strip 14.

A function of the latching strip 14 will be described below, with reference to FIGS. 7A to C. FIG. 7A shows a state where the hub 2 is retracted in the shield tube 4a to some extent from the state of FIG. 6A. FIG. 7B is a cross-sectional view taken along the line C-C of FIG. 7A. FIG. 7C is a cross-sectional view of the shield tube 4a taken along the line D-D of FIG. 7A. As shown by FIG. 7B only, an annular groove 2a is formed on an outer surface of the hub 2. In the state shown in FIGS. 7A to C, a position of the annular groove 2a coincides with the position of the engagement hole 13.

As shown in these drawings, the latching strip 14 can be wrapped around the shield tube 4a by virtue of its flexibility. As a result of the wrapping of the latching strip 14 around the shield tube 4a, the protrusion 14a protrudes into the inner bore of the shield tube 4a through the engagement hole 13. Thereby, a front end portion of the protrusion 14a engages with the annular groove 2a, thus obtaining a function of latching the hub 2 with respect to the shield tube 4a. Note here that the annular groove 2a is not necessarily required. That is to say, by contacting the front end of the protrusion 14a with the outer surface of the hub 2 so as to apply pressure thereto, the hub 2 can be held by the frictional force.

Furthermore, in the above-mentioned state, as clearly shown by FIG. 7C, the engagement hole 14c at the front end portion of the latching strip 14 engages with the fixing protrusion 15. Thereby, the wrapped state of the latching strip 14 around the shield tube 4a can be held.

The above-stated holding mechanism is provided for the following reasons: that is, in the state of FIG. 6A, the rotational position of the protrusion 11 coincides with the gate groove 12, so that the hub 2 can move toward the rear end side of the shield tube 4a. Meanwhile, there is a case where the needle 1 should be held at such an angle, and therefore, in order to latch the hub 2 with respect to the shield tube 4a in this state so as to prevent the needle 1 from retracting in the shield tube 4a, the holding mechanism is provided. Alternatively, there is another case where the hub 2 should be latched to the shield tube 4a in the state shown in FIG. 7A. This is because, in this state, the protrusion 11 is inside the gate groove 12a, and therefore the rotation of the hub 2 and the needle 1 can be limited.

Note here that, a configuration for engaging the hub 2 with the protrusion 14a of the latching strip 14 is not limited to the above configuration that uses the engagement hole 13. Instead, the latching strip 14 may be provided at a different position from the engagement hole 13 and a through hole may be provided separately so as to allow the protrusion 14a to protrude into the shield tube 4a.

Embodiment 2

Figure 8:
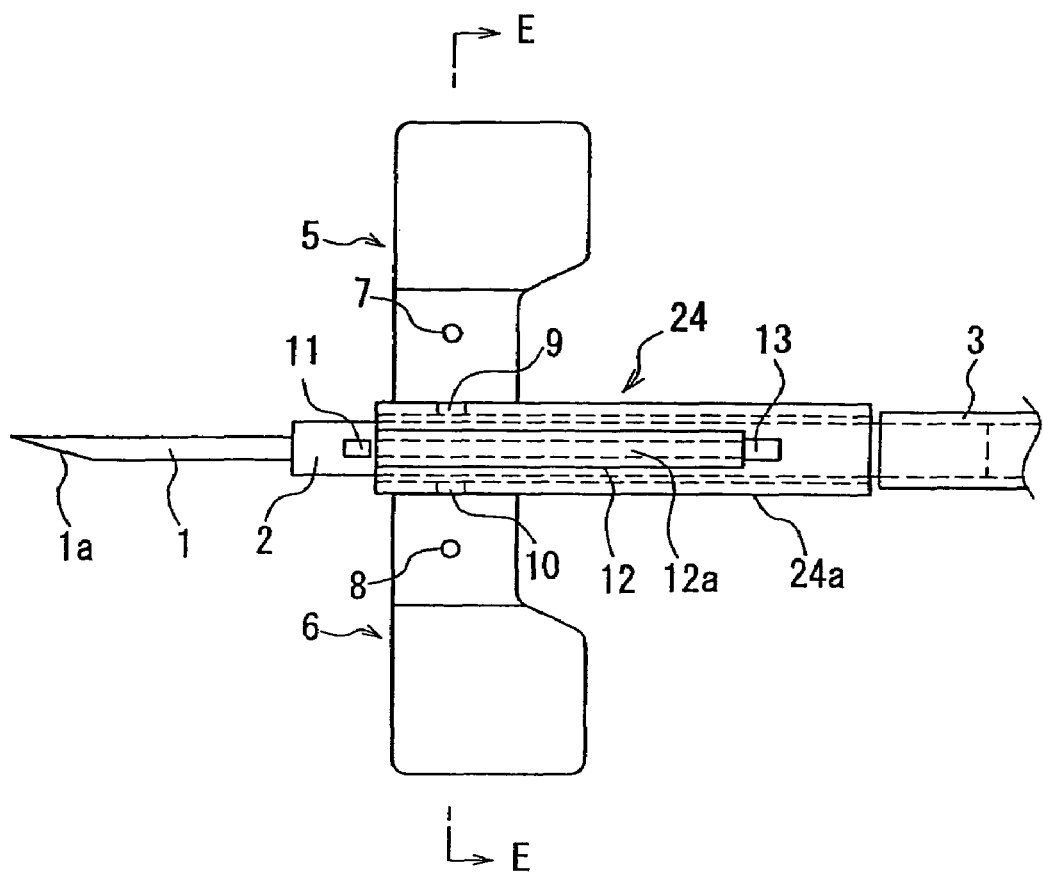
FIG. 8 is a plan view of a winged medical needle device according to Embodiment 2 of the present invention.
Figure 9:
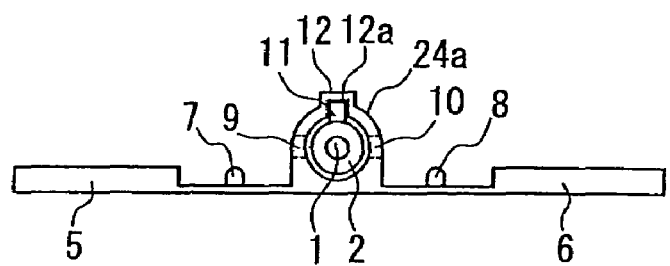
FIG. 9 is a side view of the same medical needle device from a left side of FIG. 8.
Figure 10:
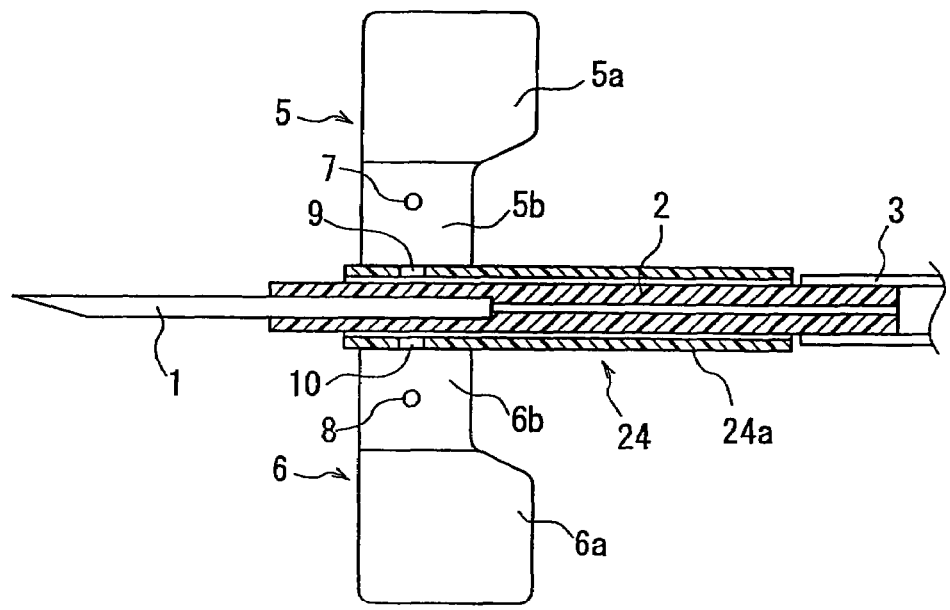
FIG. 10 is a cross-sectional view showing a planar shape of the same medical needle device.

FIG. 8 is a plan view of a medical needle device according to Embodiment 2 of the present invention, and FIG. 9 is a side view of the medical needle device from a left side of FIG. 8. FIG. 10 is a cross-sectional view showing a planar shape of the same device. This embodiment relates to a configuration having a winged shield, in which left and right wings are given to the shield tube 4a of Embodiment 1. The basic configurations of the shield tube and the hub are the same as in Embodiment 1. Therefore, the elements that are the same as those in Embodiment 1 are given the same reference numerals for their explanations.

Reference numeral 1 denotes a needle, which is fixed to a front end portion of a hub 2 made of resin. A tube 3 is connected to a rear end portion of the hub 2. Reference numeral 24 denotes a winged shield, including a shield tube 24a made of resin and having a substantially cylindrical shape, and left and right wings 5 and 6. The hub 2 has a length such that a front end portion and a rear end portion thereof can protrude from the shield tube 4a when the hub 2 is inserted into an inner bore of the shield tube 24a. An outer diameter of the hub 2 has a size such that a slight gap can be formed between the hub 2 and an inner wall of the shield tube 24a so as to allow the rotation of the hub 2 with respect to the shield tube 24a and the movement of the hub 2 in an axial direction.

The left and right wings 5 and 6 are provided at a front end portion of the shield tube 24a, that is, at an end portion of the shield tube 24a on a side from which the needle 1 protrudes. The wings 5 and 6 are coupled to both side portions of an outer peripheral surface of the shield tube 24a, respectively, and may have a symmetric shape with respect to the axis of the shield tube 24a in the center. At base regions of the wings 5 and 6, wing protrusions 7 and 8 are formed respectively. On left and right side walls of the shield tube 24a, through holes 9 and 10 are formed so as to correspond to the wing protrusions 7 and 8, respectively.

On the front end portion of the hub 2 that is exposed from a front end of the shield tube 24a, a protrusion 11 is formed at a portion of its outer peripheral surface. On an outer surface of the shield tube 24a, a ridge portion 12 is formed, and on an inner wall of the ridge portion 12, a gate groove 12a is formed. The configurations and effects of the protrusion 11, the gate groove 12a and the like are substantially the same as in Embodiment 1.

The protrusion 11 is provided at a position that does not correspond to a side of a blade surface 1a of the needle 1 and its reverse side in the circumferential direction of the hub 2. Therefore, this configuration can prevent the protrusion 11 from facing the gate groove 12a in a state where the blade surface 1a faces toward a direction perpendicular to the wings 5 and 6. Normally, at the time of puncturing, the blade surface 1a is set so as to face toward the direction perpendicular to the wings 5 and 6, and therefore this configuration can prevent the needle 1 from being pushed into the shield tube 24a during the puncturing.

Figure 11A:
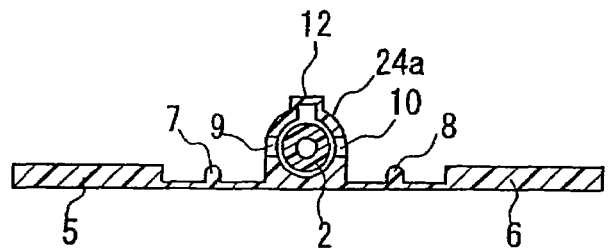
FIG. 11A is a cross-sectional view taken along the line E-E of FIG. 8.
Figure 11B:
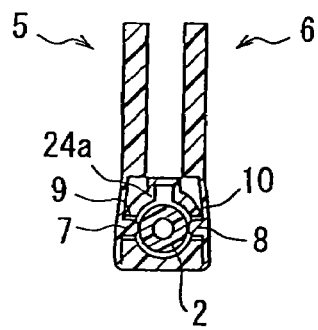
FIG. 11B is a cross-sectional view showing an operation, following the state of FIG. 11A.

FIGS. 11A and 11B show the function of the wing protrusions 7 and 8 provided on the wings 5 and 6. FIGS. 11A and 11B are cross-sectional views taken along E-E of FIG. 8. The action utilizing the wings 5 and 6 is carried out in the course of puncturing.

From the state shown in FIG. 11A, the wings 5 and 6 are lifted upwards along the outer surface of the shield tube 24a, so that, as shown in FIG. 11B, the wing protrusions 7 and 8 are inserted into the through holes 9 and 10, extend through the wall of the shield tube 24a, and protrude into the inner bore. As a result, the front end portions of the wing protrusions 7 and 8 contact with the outer surface of the hub 2. By the frictional force resulting from the pressure of the contact, the hub 2, and therefore the needle 1, can be held with respect to the winged shield 24. Therefore, the puncturing action can be carried out while the needle 1 can be held securely. Also, by pressing the two wings 5 and 6 together with fingers, a sufficient compressive force can be applied to the wing protrusions 7 and 8 so as to hold the hub 2 firmly.

Note here that it is preferable that a bottom portion of the outer surface of the shield tube 24a is made flat, so that it can be positioned securely on the patient's skin. In the drawings, the inner bore of the shield tube 24a is circular, but it is also possible that the upper side of the inner bore is provided with a curved surface corresponding to the outer surface shape of the hub 2, and that a bottom portion of the inner bore surface is flat.

According to the medical needle device having a shield for the reduction of needlestick injuries, in the state of the needle protruding from the shield so as to enable the puncturing action, the needle can be held so as not to move in the shield. Moreover, in that state, the needle can rotate with respect to the shield.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A medical needle device having a shield for reduction of needlestick injuries, comprising:
    the shield for reduction of needlestick injuries including a substantially cylindrical shield tube as a main body;
    a hub inserted into the shield tube so that the hub is movable in an axial direction and whose rear end portion can be connected to an infusion tube; and
    a needle mounted to a front end portion of the hub, wherein a tip of the needle can be stored in an inner bore of the shield tube,
    wherein the hub has a protrusion at a portion of an outer peripheral surface at a front end portion thereof, a height of the protrusion being such that the protrusion protrudes beyond an inner diameter of the shield tube, and a gate groove is formed at an inner surface of the shield tube as a stripe shaped recess so as not to pass entirely through the wall of the shield tube and so as to extend from a distal end to the vicinity of a rear end of the shield tube, the gate groove having dimensions such that the protrusion at the front end portion of the hub can fit in a front end portion of the gate groove,
    in a state where the protrusion is exposed from the front end of the shield tube, the hub can rotate around an axis of the shield tube,
    at a rotational position of the protrusion at which it does not face a front end of the gate groove, a position of the hub is limited so as not to move toward a rear end side of the shield tube due to engagement of the protrusion with a front end face of the shield tube, and
    at a rotational position of the protrusion at which it faces the front end of the gate groove, the protrusion can slide into the gate groove.

2. The medical needle device having a shield for reduction of needlestick injuries according to claim 1,
    wherein the shield tube has an engagement hole that is formed adjacent to a rear end of the gate groove, a depth of the gate groove being set so as to be shallower than the height of the protrusion at a rear end portion of the gate groove, and the protrusion can slide along the gate groove so as to engage with the engagement hole.

3. The medical needle device having a shield for reduction of needlestick injuries according to claim 1, wherein the protrusion is provided at a position that does not correspond to a side of a blade surface of the needle and its reverse side in a circumferential direction of the hub.

4. The medical needle device having a shield for reduction of needlestick injuries according to claim 1, wherein the protrusion is provided at a position that corresponds to a side of a blade surface of the needle in a circumferential direction of the hub.

5. The medical needle device having a shield for reduction of needlestick injuries according to claim 1, further comprising: a latching strip having flexibility, provided so as to extend from a side wall of the shield tube; and a through hole provided in the shield tube so as to correspond to a position of the latching strip,
    wherein the latching strip has a protrusion protruding toward a side direction, and
    when the latching strip is wrapped around the shield tube, the protrusion is inserted into the through hole so as to limit movement of the hub in the axial direction within the shield tube.

6. The medical needle device having a shield for reduction of needlestick injuries according to claim 5, wherein the latching strip has a mechanism for holding the latching strip, functioning so as to hold the wrapped state of the latching strip around the shield tube.

7. The medical needle device having a shield for reduction of needlestick injuries according to claim 1, the shield for reduction of needlestick injuries is a winged shield that further comprises a pair of wings coupled near the front end of the shield tube.

8. The medical needle device having a shield for reduction of needlestick injuries according to claim 7,
    wherein each of the wings has a wing protrusion formed so as to protrude from a wing surface,
    the shield tube has through holes formed on side portions of a cylindrical wall so that the wing protrusions can be inserted in the respective through holes, and
    by superimposing both of the wings on the shield tube along a side surface of the shield tube, each wing protrusion can pass through the through hole so as to be inserted into the inner bore of the shield tube, so that each wing protrusion prevents the hub from moving in the axial direction within the shield tube, and so that the hub can be held with respect to the shield tube while keeping a state in which the needle protrudes from the front end of the shield tube by a predetermined length.

* * * * *